US007993865B2

(12) United States Patent
Targan et al.

(10) Patent No.: US 7,993,865 B2
(45) Date of Patent: *Aug. 9, 2011

(54) DIAGNOSIS, PREVENTION AND TREATMENT OF CROHN'S DISEASE USING THE OMPC ANTIGEN

(75) Inventors: Stephan R. Targan, Santa Monica, CA (US); Jonathan Braun, Tarzana, CA (US); Christopher L. Sutton, Encinitas, CA (US)

(73) Assignees: Cedars-Sinai Medical Center, Los Angeles, CA (US); The Regents of the University of California, Oakland, CA (US)

( * ) Notice: Subject to any disclaimer, the term of this patent is extended or adjusted under 35 U.S.C. 154(b) by 621 days.

This patent is subject to a terminal disclaimer.

(21) Appl. No.: 11/561,024

(22) Filed: Nov. 17, 2006

(65) Prior Publication Data

US 2007/0161065 A1 Jul. 12, 2007

Related U.S. Application Data

(63) Continuation of application No. 09/575,061, filed on May 19, 2000, now Pat. No. 7,138,237.

(51) Int. Cl.
*G01N 33/564* (2006.01)
*G01N 33/569* (2006.01)

(52) U.S. Cl. ............ 435/7.32; 435/4; 435/7.1; 435/7.2; 435/7.92; 435/287.2; 435/288.3; 436/506; 436/512; 436/513; 436/518; 436/811; 422/73; 422/82.05; 422/91; 422/430

(58) Field of Classification Search ............... 435/4, 7.1, 435/7.2, 7.32, 7.92, 287.2, 288.3; 436/506, 436/512, 513, 518, 811; 422/61, 73, 82.05, 422/91, 430
See application file for complete search history.

(56) References Cited

U.S. PATENT DOCUMENTS

| | | | |
|---|---|---|---|
| 4,444,879 A * | 4/1984 | Foster et al. | ................. 435/7.95 |
| 5,681,699 A | 10/1997 | Rotter et al. | |
| 5,691,151 A | 11/1997 | Braun et al. | |
| 5,874,233 A | 2/1999 | Targan et al. | |
| 5,916,748 A | 6/1999 | Targan et al. | |
| 5,932,429 A | 8/1999 | Targan et al. | |
| 5,968,741 A | 10/1999 | Plevy et al. | |
| 6,033,864 A * | 3/2000 | Braun et al. | ................... 435/7.1 |

(Continued)

FOREIGN PATENT DOCUMENTS
WO        WO99 45955        3/1999

OTHER PUBLICATIONS

Lindberg et al., Antibody IgG, IgA, and IgM) to baker's yeast (*Saccharomyces cerevisiae*), yeast mannan, gliadin, ovalbumin, and betalactoglobulin in monozygotic twins with Inflammatory Bowel Disease, Gut 33: 909-913 (1992).*

(Continued)

*Primary Examiner* — Gail R Gabel
(74) *Attorney, Agent, or Firm* — Kilpatrick, Townsend & Stockton LLP

(57) ABSTRACT

The present invention provides a method of diagnosing Crohn's disease in a subject by determining the presence or absence or IgA anti-OmpC antibodies in the subject, where the presence of the IgA anti-OmpC antibodies indicates that the subject has Crohn's disease.

11 Claims, 5 Drawing Sheets

U.S. PATENT DOCUMENTS

| | | | |
|---|---|---|---|
| 6,218,129 | B1 | 4/2001 | Walsh et al. |
| 2007/0161065 | A1 | 7/2007 | Targan et al. |
| 2009/0221006 | A1* | 9/2009 | Targan et al. ............. 435/7.91 |
| 2009/0221007 | A1* | 9/2009 | Targan et al. ............. 435/7.91 |

OTHER PUBLICATIONS

Accession No. CAB07159, Hypothtical protein Rv3557c (*Mycobacterium tuberculosis*), 1998.
Accession No. P39897, Regulatory Protein MTRR, (1994).
Accession No. S38906, Hypothetical protein 4- *Clostridium pasteurianum*, (1995).
Accession No. AF173683, Bacterium I2 unknow gene, (1999).
Blaser, et al., *Gastroenterology*, 87:888-894, (1984).
Brandwein, et al., *J. Immunol.*, 159:44-52 (1997).
Breeling, et al., *Infection and Immunity*, 56:1754-1759 (1988).
Broekroelofs, et al., *Dig. Dis. Sci.*, 39:545-549, (1994).
Cambridge, et al., *Gut*, 33:668-674, (1992).
Cellier, et al., *Gastroenterol. Clin. Biol.*, 22:675-678, (1998).
Chang, et al., *Science*, 266:1865-1869, (1994).
Chiba, et al., *J. Gastroenterology*, 33:482-487 (1998).
Clarkston, et al., *Dis. Colon Rectum*, 41:195-199 (1998).
Cocito, et al., *Clinical Microbiology Reviews*, 7(3):328-345 (1994).
Cohavy, et al., *Infection and Immunity*, 68:1542-1548 (2000).
Cohavy, et al., *Infection and Immunity*, 67:6510-6517 (1999).
Cohavy, et al., *FASEB J.*, 12(4):A593, Abstract 3446 (1998).
Cong et al., *J. Exp. Med.*, 187:855-864 (1998).
Dalwadi, et al., *Gastroeneterology*, 116(4):A696 AGA Abstracts (1999).
Dalwadi, et al., *Current Opinion in Gastroenterology*; 16:56-59 (2000).
Davidson et al., *Clin. Exp. Immunol.*, 35:147-148 (1979).
Del Prete, et al., *J. Microbiol. Methods*, 33:105-114 (1998).
Delcour, *FEMS Microbiology Letters*, 151:115-123 (1997).
Dianda et al., *Am. J. Pathol.*, 150:91-97 (1997).
Duchene, et-al., *Journal of Bacteriology*, 170:155-162 (1988).
Duchmann, et al., *Scand. J. Immunol.*, 44:71-79 (1996).
El-Zaatari, et al., *Journal of Clinical Microbiology*, 35(7):1794-1799 (1997).
El-Zaatari, et al., *Current Microbiology*, 29:177-184 (1994).
Elsaghier, et al., *Clin. Exp. Immunol.* 90:503-508 (1992).
Faille, et al., *Eur. J. Microbiol. Infect. Dis.*, 11:438-445 (1992).
Fidler, et al., *Gut*, 35:506-510 (1994).
Gui, et al., *J. Antimicrob. Chemother.*, 39:393-400 (1997).
Herfarth, et al., *Gut*, 39:836-845 (1996).
Janowitz, et al., *Inflamm. Bowel. Dis.*, 4:29-39 (1998).
Knoflach, et al., *Gastroenterology*, 92:479-485 (1987).
Lindberg, et al., *Gut*, 33:909-913 (1992).
Lodish, et al., *Molecular Cell biology*, Chapter 14 (1995).
MacPherson et al., *Gut*, 38:365-375 (1996).
Metcalf, *Brit. Med. J.*, 316:166 (1998).
Mizuno, et al., *J. Biol. Chem.*, 258:6932-3640 (1983).
Morrissey, et al., *J. Exp. Med.*, 178:237-244 (1993).
Moss et al., *Gut*, 33:1209-1213 (1992).
Oh, et al., *Gastroenterology*, 120 Supplement 1419, (2001).
Pool, et al., *Gut*, 34:46-50 (1993).
Poxton, et al., *J. Med. Microbiol.*, 46:85-91 (1997).
Prantera, *Am. J. Gastroenterol.*, 91:328-332 (1996).
Pratt, et al., *Mol. Mirco.*, 20:911-917 (1996).
Rath, et al., *The Journal of Clinical Investigation*, 98:945-953 (1996).
Rowbotham, et al., *Clin. Exp. Immunol.*, 102:456-461 (1995).
Rudpolphi, et al., *Eur. J. Immunol.*, 26:1156-1163 (1996).
Sanderson et al., *Gut* 33:890-896 (1992).
Sartor, *The American Journal of Gastroenterology*, 92:5S-11S (1997).
Saxon, et al., *J. Allergy Clin. Immunol.*, 86:202-210 (1990).
Schlesinger, et al., *J. Amer. Medical Association*, 267:1489-1494 (1992).
Seibold, et al., *Journal of Clinical Immunology*, 16(2):153-160 (1998).
Sendid, et al., *Clin. Diag. Lab. Immunol.*, 3:219-226 (1996).
Sobajima, et al., *Clinical and Experimental Immunology*, 107:135-140 (1997).
Sonnenberg, *Gut*, 31:1037-1040 (1990).
Sutton, et al., *Gastroenterology*, 119:23-31 (2000).
Targan, et al., *Gastroenterology*, 122:supplement S1176 (2002).
Thomas, et al., *Gut*, 42:497-500 (1998).
Vannuffel, et al., *Clinical and Diagnostic Laboratory Immunology*, 1(2):241-243 (1994).
Vermeire, et al., *Gastroenterological Assoc. Dig. Disease Week*, 120:supplement 1418 (2001).
Wayne, et al., *Journal of Clinical Microbiology*, 30(8):2013-2018 (1992).
Weiner, *Hospital Practice*, 53-58 (1995).
Weiner, et al., *Ann. Rev. Immunol.*, 12:809-837 (1994).
Wexler, *Clinical Infectious Diseases*, 25(Suppl 2):S284-S286 (1997).
Joosens, et al., *Digestive Disease Week Abstracts and Itinerary Planner*; vol. 2003, pp. Abstract No. M1174.
Zhouludev at al., *American Journal of Gastroenterology*; Vo. 99, No. 11, pp. 2235-2241 (Abstract), (2004).

\* cited by examiner

E. coli 367 amino acids outer membrane protein c precursor:

```
  1 mkskvlalli pallaagaah aaevynkdgn kldlygkvdg lhyfsdnkdv dgdqtymrlg
 61 fkgetqvtdq ltgyggweyq iqgnsaenen nswtrvafag lkfqdvgsfd ygrnygvvyd
121 vtswtdvlpe fggdtygsdn fmqqrgnfga tyrntdffgl vdglnfavqy qgkngnpsge
181 gftsgvtnng rdalrqngdg vggsitydye gfgiggaiss skrtdaqnta ayigngdrae
241 tytgglkyda nniylaaqyt qtynatrvgs lgwankaqnf eavaqyqfdf glrpslaylq
301 skgknlgrgy ddedilkyvd vgatyyfnkn mstyvdykin llddnqftrd agintdniva
361 lglvyqf    (SEQ ID NO:1)
```

FIG. 5

```
  A  GAT CTG GCC AGC GCC GTG GGC ATC CAG TCC GGC AGC ATC TTT CAT CAC TTC AAG AGC AAG
▲ D    L   A   S   A   V   G   I   Q   S   G   S   I   F   H   H   F   K   S   K
  GAT GAG ATA TTG CGT GAG GCG ATG GAG GTG ATG ACG GAA CGC ATC TAC AAC ACC GCG ATG CGC
▲ D   E   I   L   R   E   A   M   E   V   M   T   E   R   I   Y   N   T   A   M   R
  GCT TCA CTG GAG GAA GCA TCG ACG AGT GGC GAG GCC ATG GCG CTG GTC ATC CGC TGC GAG
▲ A   S   L   E   E   A   S   T   V   R   E   R   V   L   A   L   I   R   C   E
  TTG CAG TCG ATC ATG GGC GGC AGC CAC GCG GCC CTG GTC CGT GAC GTG TAT GAG TGG CGC
▲ L   Q   S   I   M   G   G   S   H   A   A   L   V   R   D   V   L   V   E   W   R
  TCG CTG TCG GCC GAA GGC CAG GCG CAC GTG GCG CTG CGT GAC GTG TAT GAG CAG ATC T   (SEQ ID NO:3)
▲ S   L   S   A   E   G   Q   A   H   V   A   L   R   D   V   Y   E   Q   I        (SEQ ID NO:2)
```

FIG. 6

DIAGNOSIS, PREVENTION AND TREATMENT OF CROHN'S DISEASE USING THE OMPC ANTIGEN

This invention was made with Government support under Grant No. DK046763 awarded by the National Institutes of Health. The Government has certain rights in this invention.

BACKGROUND OF THE INVENTION

1. Field of the Invention

The invention relates generally to the fields of immunology and inflammatory bowel disease and more specifically to the diagnosis and treatment of Crohn's disease using the bacterial antigen, outer membrane protein C (OmpC).

2. Background Information

Inflammatory bowel disease (IBD) is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. Onset of IBD is predominantly in young adulthood with diarrhea, abdominal pain, and fever the three most common presenting symptoms. The diarrhea may range from mild to severe, and anemia and weight loss are additional common signs of IBD. Ten percent to fifteen percent of all patients with IBD will require surgery over a ten year period. In addition, patients with IBD are at increased risk for the development of intestinal cancer. Reports of an increased occurrence of psychological problems, including anxiety and depression, are perhaps not surprising symptoms of what is often a debilitating disease that strikes people in the prime of life.

Unfortunately, the available therapies for inflammatory bowel disease are few, and both diagnosis and treatment have been hampered by a lack of knowledge regarding the etiology of the disease. What is clear, however, is that a combination of genetic factors, exogenous triggers and endogenous microflora can contribute to the immune-mediated damage to the intestinal mucosa seen in inflammatory bowel disease. In Crohn's disease, bacteria have been implicated in initiation and progression of the disease: the intestinal inflammation in Crohn's disease is notable for its frequent responsiveness to antibiotics and susceptibility to bacterial fecal flow. Common intestinal colonists and novel pathogens have been implicated in Crohn's by direct detection or by disease associated antimicrobial immune responses. Furthermore, in many genetically susceptible animal models of chronic colitis, lumenal micro-organisms are a necessary cofactor for disease; animals housed in a germ-free environment do not develop colitis. However, despite much direct and indirect evidence for a role for enteric microorganisms in Crohn's disease, the pathogenic organisms and antigens contributing to the immune dysregulation seen in this disease have not been identified.

Current diagnostic assays for Crohn's disease are unable to detect all patients with the disease. Thus, identification of novel microbial antigens associated with Crohn's disease would provide reagents that can increase the sensitivity of current diagnostic assays. In addition, such microbial antigens can bear a disease related T-cell epitope and, as original or contributing inducers of the disease-related immune response, can be effective tolerogenic antigens for treating Crohn's disease.

Thus, there is a need for identification of microbial antigens associated with Crohn's disease that can be used to improve the sensitivity of current diagnostic assays for this disease. The present invention satisfies this need and provides related advantages as well.

SUMMARY OF THE INVENTION

The present invention provides a method of diagnosing Crohn's disease in a subject by determining the presence or absence of IgA anti-outer membrane protein C (OmpC) antibodies in the subject, where the presence of the IgA anti-OmpC antibodies indicates that the subject has Crohn's disease. A method of the invention can be practiced, for example, by obtaining a sample from a subject; contacting the sample with an OmpC antigen, or reactive fragment thereof, under conditions suitable to form a complex of the OmpC antigen, or reactive fragment thereof, and IgA antibody to the OmpC antigen; contacting the complex with an anti-IgA antibody; and detecting the presence or absence of IgA anti-OmpC antibodies, where the presence of the IgA anti-OmpC antibodies in the subject indicates that the subject has Crohn's disease. In one embodiment, the invention is practiced using an OmpC antigen having substantially the amino acid sequence of SEQ ID NO: 1. In another embodiment, the IgA anti-OmpC antibodies are detected with an enzyme-linked immunosorbent assay.

The invention further provides a method of diagnosing Crohn's disease by determining the presence or absence of IgA anti-OmpC antibodies in the subject and the presence or absence of IgA anti-*Saccharomyces cerevisiae* antibodies (ASCA) in the subject, where the presence of IgA anti-OmpC antibodies or the presence of IgA ASCA in the subject each independently indicates that the subject has Crohn's disease. The presence of IgA ASCA can be determined, for example, by reactivity with purified yeast cell wall phosphopeptidomannan (PPM), which can be prepared, for example, from ATCC strain #38926.

The invention additionally provides a method of diagnosing Crohn's disease by determining the presence or absence of IgA anti-OmpC antibodies in the subject and the presence or absence of IgA anti-I-2 polypeptide antibodies in the subject, where the presence of IgA anti-OmpC antibodies or the presence of IgA anti-I-2 polypeptide antibodies in the subject each independently indicates that the subject has Crohn's disease. In one embodiment, the presence of IgA anti-I-2 polypeptide antibodies is determined by IgA reactivity against an I-2 polypeptide having substantially the amino acid sequence of SEQ ID NO: 3.

Further provided by the invention is a method of diagnosing Crohn's disease in a subject by determining the presence or absence of IgA anti-OmpC antibodies in the subject; determining the presence or absence of IgA ASCA in the subject; and determining the presence or absence of IgA anti-I-2 polypeptide antibodies in the subject, where the presence of the IgA anti-OmpC antibodies, the presence of IgA ASCA or the presence of IgA anti-I-2 polypeptide antibodies each independently indicates that the subject has Crohn's disease. In one embodiment, this method further includes the step of determining the presence or absence of perinuclear anti-neutrophil antibodies (pANCA) in the subject.

The invention further provides a method of inducing tolerance in a patient with Crohn's disease by administering an effective dose of an OmpC antigen, or tolerogenic fragment thereof, to the patient with Crohn's disease. An OmpC antigen useful in a method of inducing tolerance can have, for example, substantially the amino acid sequence of SEQ ID NO: 1.

BRIEF DESCRIPTION OF THE DRAWINGS

FIG. 5 shows the E. coli OmpC amino acid sequence (SEQ ID NO: 1).

FIG. 6 shows the I-2 nucleotide sequence (SEQ ID NO: 2) and predicted amino acid sequence (SEQ ID NO: 3).

DETAILED DESCRIPTION OF THE INVENTION

Figure 1:
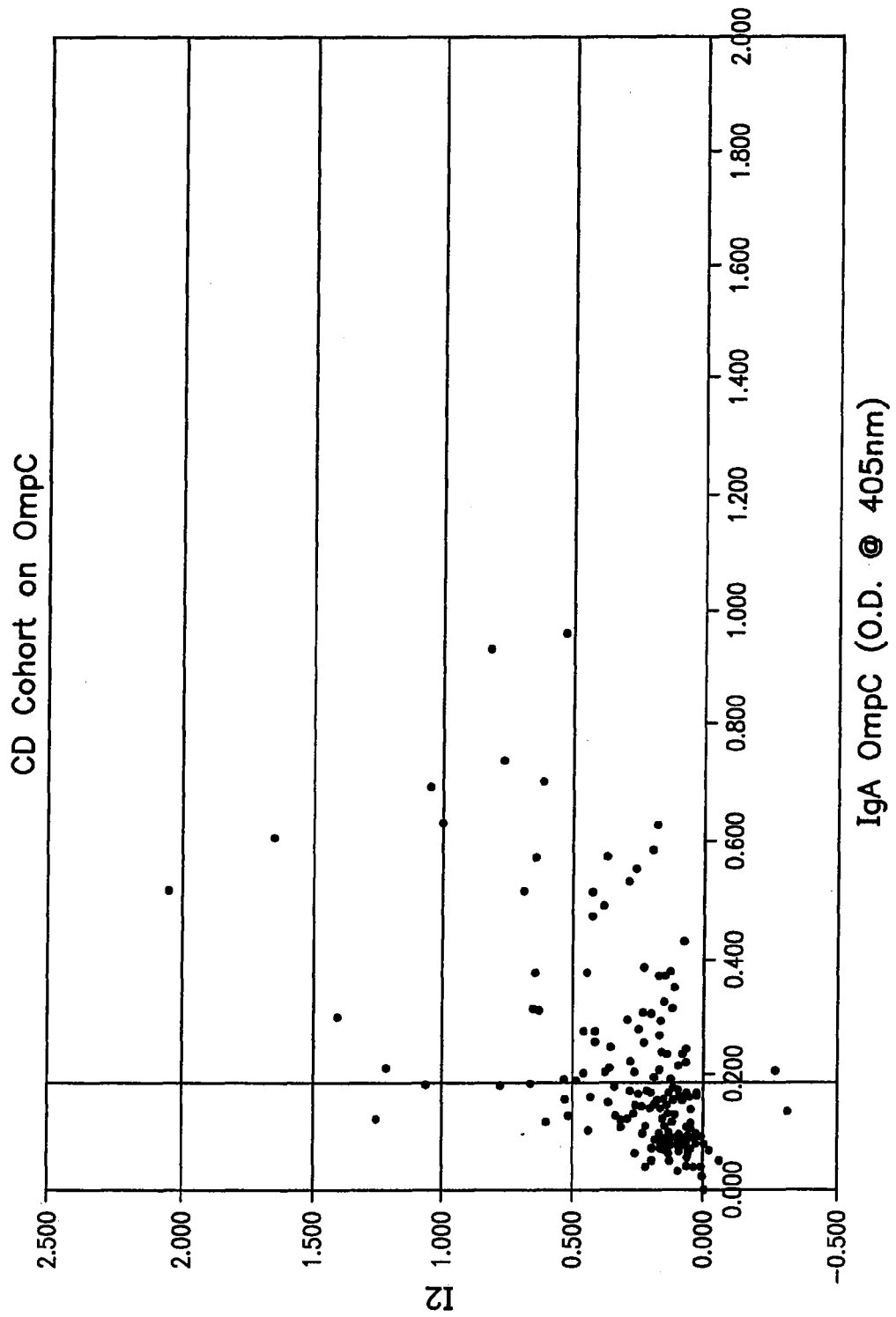
FIG. 1 shows the IgA OmpC reactivity and IgA I-2 reactivity of sera from patients having Crohn's disease.
Figure 2:
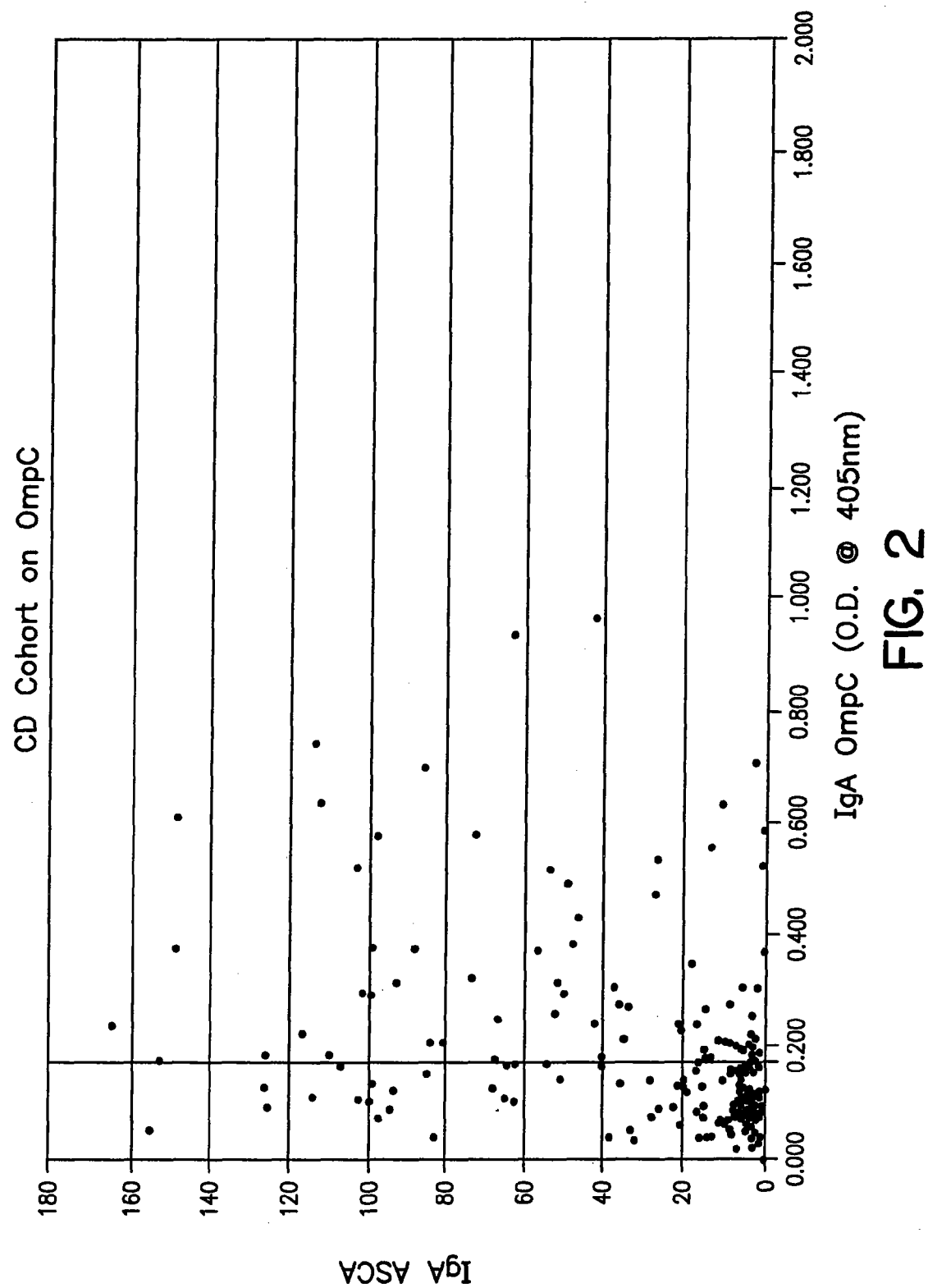
FIG. 2 shows IgA OmpC reactivity and IgA ASCA reactivity of sera from patients having Crohn's disease.
Figure 3:
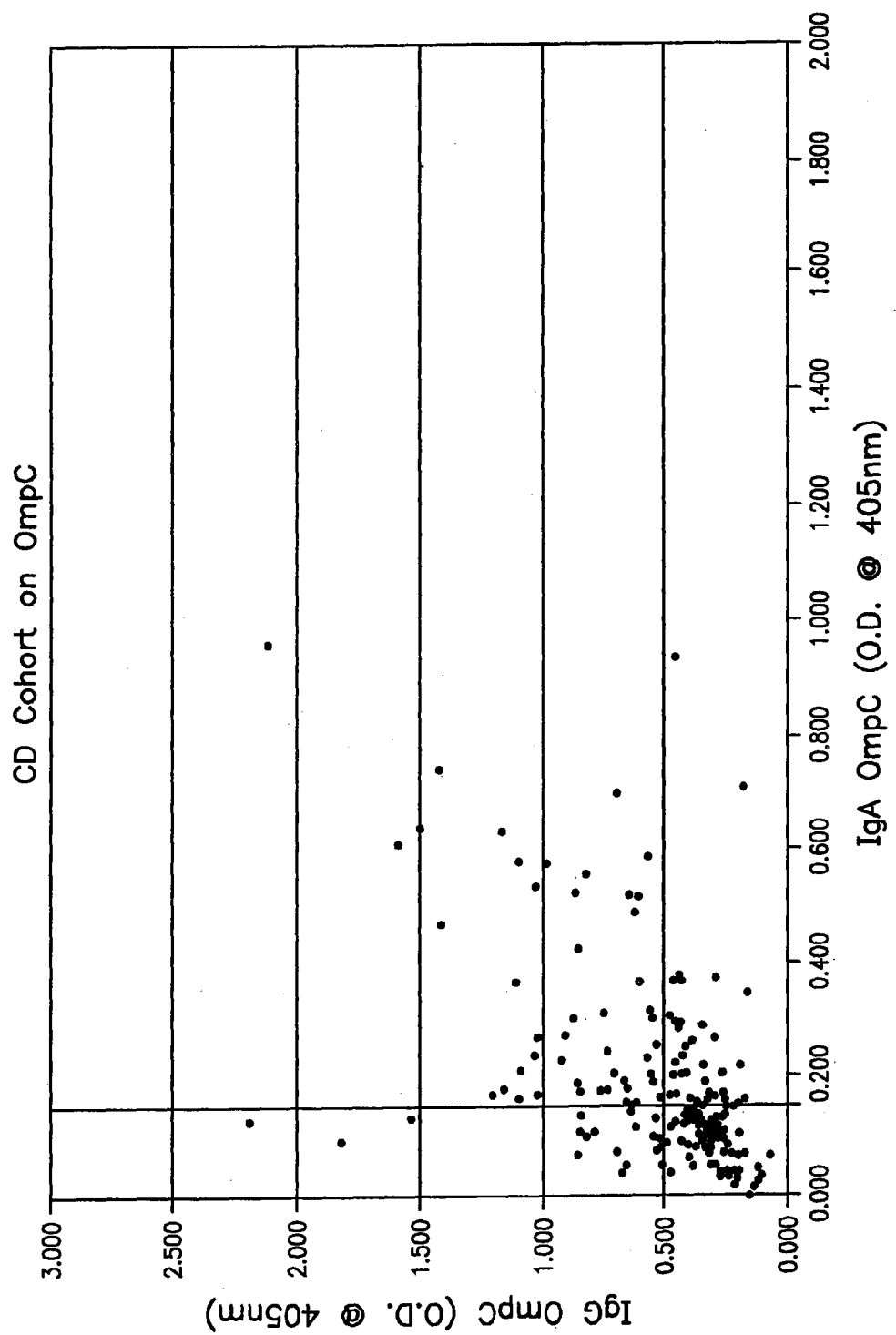
FIG. 3 shows IgA OmpC reactivity and IgG OmpC reactivity of sera from patients having Crohn's disease.
Figure 4:
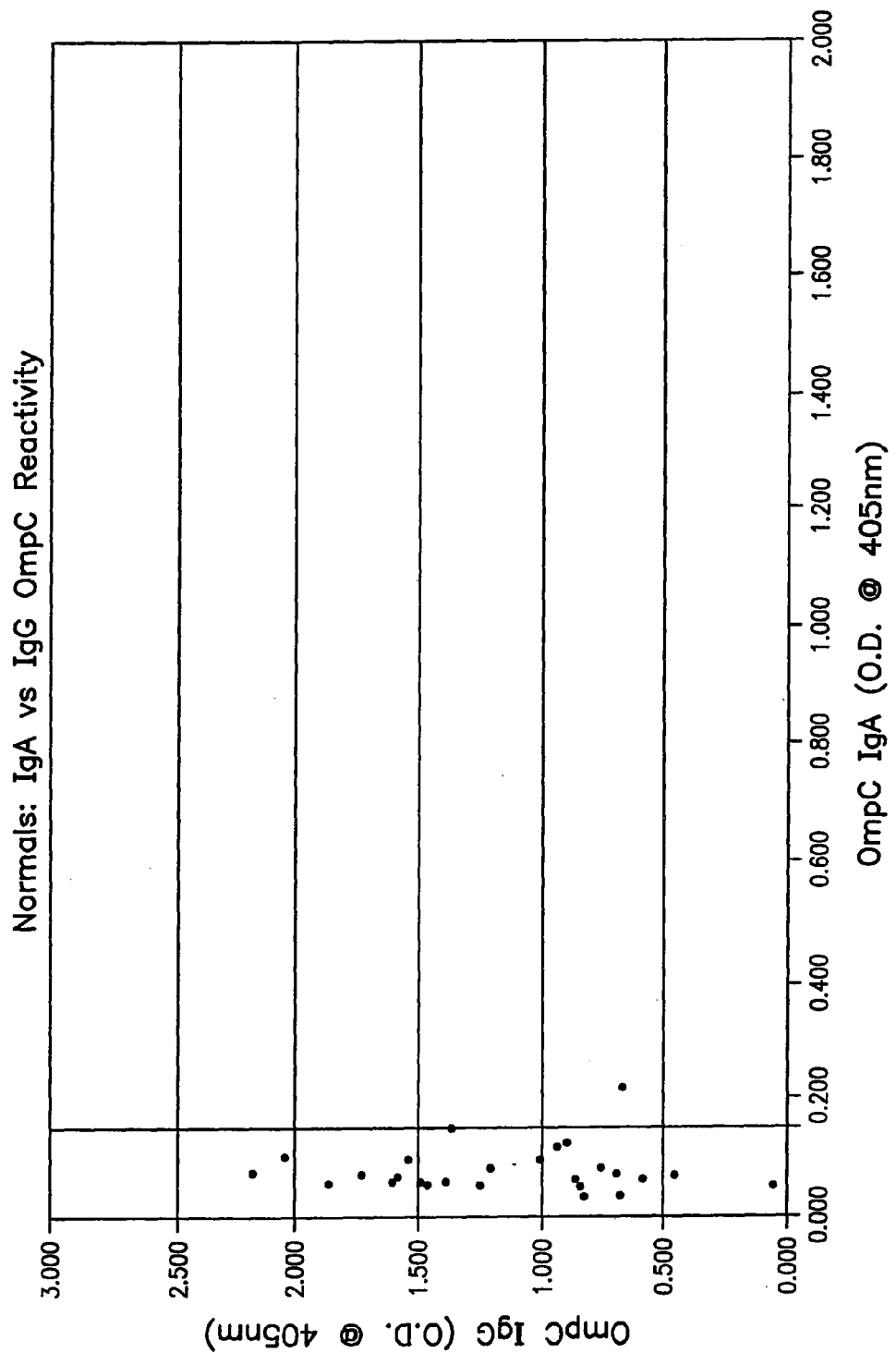
FIG. 4 shows IgA and IgG OmpC reactivity of sera from normal individuals.

The present invention is directed to the exciting discovery that IgA antibodies to outer membrane protein C (OmpC) are associated with Crohn's disease. As shown in FIG. 4, only a single individual without Crohn's disease ("normal") had IgA OmpC reactivity greater than $0.2_{405}$, although many normals showed significant IgG OmpC reactivity. In contrast to the normals, significant IgA OmpC reactivity was present in sera from many patients having Crohn's disease (see FIG. 1). Furthermore, this reactivity was apparently distinct, in large part, from IgA I-2 and IgA ASCA reactivity seen in sera from Crohn's disease patients (FIGS. 1 and 2). These results are summarized in Table 1, which indicates that IgA OmpC reactivity together with IgA ASCA reactivity, pANCA reactivity and I-2 polypeptide reactivity is a highly sensitive diagnostic system which can detect 86% of patients with Crohn's disease. Furthermore, as shown in Table 2, IgA OmpC reactivity itself detected 55% of patients having Crohn's disease. These results indicate that IgA OmpC reactivity can be valuable in increasing the number of Crohn's disease patients that are diagnosed with the disease, thereby facilitating earlier and more appropriate treatment.

TABLE 1

CD COHORT

|  | Total | ASCA Panel+ | IqA OmpC+ | pANCA | I2 | Additional % Detected | Cumulative % Detected |
|---|---|---|---|---|---|---|---|
| CD Cohort | 153 | 86 |  |  |  | 56% | 56% |
| ASCA Panel− | 67 |  | 31 |  |  | 20% | 76% |
| ASCA Panel−/OmpC− | 36 |  |  | 12 |  | 8% | 84% |
| ASCA Panel−/OmpC−/pANCA− | 24 |  |  |  | 2 | 1% | 86% |
| Total % Detected: |  |  |  |  |  | 86% | 86% |

TABLE 2

CD COHORT

|  | Total | ASCA Panel+ | OmpC+ | pANCA | I2 |
|---|---|---|---|---|---|
| n: | 153 | 86 | 84 | 36 | 79 |
| % detected: |  | 56% | 55% | 24% | 52% |

Based on the above, the present invention provides a method of diagnosing Crohn's disease in a subject by determining the presence or absence of IgA anti-OmpC antibodies in the subject, where the presence of the IgA anti-OmpC antibodies indicates that the subject has Crohn's disease. A method of the invention can be practiced, for example, by obtaining a sample from a subject; contacting the sample with an OmpC antigen, or reactive fragment thereof, under conditions suitable to form a complex of the OmpC antigen, or reactive fragment thereof, and IgA antibody to the OmpC antigen; contacting the complex with an anti-IgA antibody; and detecting the presence or absence of IgA anti-OmpC antibodies, where the presence of the IgA anti-OmpC antibodies in the subject indicates that the subject has Crohn's disease. In one embodiment, the invention is practiced using an OmpC antigen having substantially the amino acid sequence of SEQ ID NO: 1. In another embodiment, the IgA anti-OmpC antibodies are detected with an enzyme-linked immunosorbent assay.

The outer-membrane protein C ("OmpC") useful in the methods of the invention is a "porin," a class of transmembrane proteins that are found in the outer membranes of bacteria, including gram-negative enteric bacteria such as E. coli. The porins in the outer membrane of an E. coli cell provide channels for passage of disaccharides, phosphate and similar molecules. Porins can be trimers of identical subunits arranged to form a barrel-shaped structure with a pore at the center (Lodish et al., Molecular Cell Biology, Chapter 14 (1995)).

OmpC is one of the major porin proteins found in the outer membranes of bacteria such as E. coli. OmpC is similar in structure and function to outer-membrane protein F ("OmpF"). Both assemble as trimers in the outer membrane to form aqueous channels that allow the passive diffusion of small, hydrophilic molecules across the hydrophobic barrier. However, OmpC pores have a diameter of 1.1 nm, while OmpF pores have a diameter of 1.2 nm. This difference results in a slower rate of diffusion through the OmpC pores than through the OmpF pores.

Porin expression can be influenced by environmental conditions, including osmolarity, temperature, growth phase and toxin concentration. For example, in the intestine, where both nutrient and toxic molecule concentrations are relatively high, OmpC, with a smaller pore diameter, is the predominant porin (Pratt et al., Mol. Micro., 20:911-917 (1996)).

As used herein, the term "OmpC antigen" or "OmpC" means a protein that has linear or conformational homology to OmpC. A OmpC antigen can be derived from a gram-negative bacterium, such as E. coli, and can be a species homolog of E. coli OmpC (SEQ ID NO: 1), which is shown in FIG. 5. In nature, an OmpC antigen is a protein that forms a trimeric structure in the outer membrane of bacteria which allows the passage of small molecules, or a precursor of such a protein.

As used herein, the term OmpC antigen or OmpC means a protein that has at least 50% amino acid identity with E. coli OmpC (SEQ ID NO: 1) shown in FIG. 5. An OmpC antigen can have, for example, at least 60%, 70%, 80%, 85%, 90% or 95% amino acid identity with SEQ ID NO: 1, said amino acid identity determined with CLUSTALW using the BLOSUM 62 matrix with default parameters. For use in the methods of the invention, an OmpC antigen can be partially purified, for example, by spheroplast lysis from OmpA and OmpF deficient cells as described in Example IV, or can be similarly prepared from a variety of other *E. coli* strains, which can contain OmpA and OmpF in addition to OmpC. An OmpC antigen also can be prepared recombinantly by expressing an encoding nucleic acid sequence such as that available as GenBank accession K00541 by methods well known in the art (see, for example, Ausubel et al., *Current Protocols in Molecular Biology* John Wiley & Sons, Inc. New York (1999)).

The methods of the invention relate to determining the presence or absence of IgA anti-OmpC antibodies in a subject. As used herein, the "presence of IgA anti-OmpC antibodies" means IgA reactivity against an OmpC antigen that is greater than two standard deviations above the mean IgA anti-OmpC reactivity of control (normal) sera analyzed under the same conditions.

The methods of the invention relate to the diagnosis and treatment of Crohn's disease (regional enteritis), which is a disease of chronic inflammation that can involve any part of the gastrointestinal tract. Commonly the distal portion of the small intestine (ileum) and cecum are affected. In other cases, the disease is confined to the small intestine, colon or anorectal region. Crohn's disease occasionally involves the duodenum and stomach, and more rarely the esophagus and oral cavity.

The variable clinical manifestations of Crohn's disease are, in part, a result of the varying anatomic localization of the disease. The most frequent symptoms of Crohn's disease are abdominal pain, diarrhea and recurrent fever. Crohn's disease is commonly associated with intestinal obstruction or fistula, which is an abnormal passage between diseased loops of bowel, for example. Crohn's disease also includes complications such as inflammation of the eye, joints and skin; liver disease; kidney stones or amyloidosis. In addition, CD is associated with an increased risk of intestinal cancer.

Several features are characteristic of the pathology of Crohn's disease. The inflammation associated with CD, known as transmural inflammation, involves all layers of the bowel wall. Thickening and edema, for example, typically also appear throughout the bowel wall, with fibrosis also present in long-standing disease. The inflammation characteristic of CD also is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of CD.

A hallmark of Crohn's disease is the presence of discrete aggregations of inflammatory cells, known as granulomas, which are generally found in the submucosa. Some Crohn's disease cases display the typical discrete granulomas, while others show a diffuse granulomatous reaction or nonspecific transmural inflammation. As a result, the presence of discrete granulomas is indicative of CD, although the absence of granulomas also is consistent with the disease. Thus, transmural or discontinuous inflammation, rather than the presence of granulomas, is a preferred diagnostic indicator of Crohn's disease (Rubin and Farber, *Pathology* (Second Edition) Philadelphia: J.B. Lippincott Company (1994)).

In contrast to ulcerative colitis, which is characterized by a continuous inflammation of the colon that usually is more severe distally than proximally, Crohn's disease is a patchy disease with frequent sparing of the rectum. Furthermore, the inflammation is Crohn's disease is distinct from the superficial inflammation seen in ulcerative colitis, which is usually limited to the mucosal layer and is characterized by an acute inflammatory infiltrate with neutrophils and crypt abscesses. Instead, Crohn's disease affects the entire thickness of the bowel wall with granulomas often, although not always, present. Furthermore, involvement of the terminal ileum, a cobblestone-like appearance, discrete ulcers or fistulas suggest Crohn's disease. Characteristics that serve to distinguish Crohn's disease from ulcerative colitis are summarized in Table 3 (Rubin and Farber, supra, 1994).

TABLE 3

Characteristic Features of Crohn's disease and ulcerative colitis

| Feature | Crohn's Disease | Ulcerative Colitis |
| --- | --- | --- |
| Macroscopic | | |
| Thickened bowel wall | Typical | Uncommon |
| Luminal narrowing | Typical | Uncommon |
| "Skip" lesions | Common | Absent |
| Right colon predominance | Typical | Absent |
| Fissures and fistulas | Common | Absent |
| Circumscribed ulcers | Common | Absent |
| Confluent linear ulcers | Common | Absent |
| Pseudopolyps | Absent | Common |
| Microscopic | | |
| Transmural inflammation | Typical | Uncommon |
| Submucosal fibrosis | Typical | Absent |
| Fissures | Typical | Rare |
| Granulomas | Common | Absent |
| Crypt abscesses | Uncommon | Typical |

As used herein, the term "subject" means any animal capable of having inflammatory bowel disease, including a human, non-human primate, rabbit, rat or mouse, especially a human. A subject can have one or more symptoms of Crohn's disease or ulcerative colitis, or may be asymptomatic.

A sample useful in the methods of the invention can be obtained from any biological fluid having antibodies such as, for example, whole blood, plasma, saliva, or other bodily fluid or tissue, preferably serum.

As used herein, the term "fragment" means a peptide, polypeptide or compound containing naturally occurring amino acids, non-naturally occurring amino acids or chemically modified amino acids. A reactive fragment or tolerogenic fragment of an OmpC antigen also can be a peptide mimetic, which is a non-amino acid chemical structure that mimics the structure of a peptide having an amino acid sequence, provided that the peptidomimetic retains preferential reactivity with IgA antibodies in sera of Crohn's disease patients or tolerogenic activity, as defined herein. Such a mimetic generally is characterized as exhibiting similar physical characteristics such as size, charge or hydrophobicity in the same spatial arrangement found in its peptide counterpart. A specific example of a peptide mimetic is a compound in which the amide bond between one or more of the amino acids is replaced, for example, by a carbon-carbon bond or other bond well known in the art (see, for example, Sawyer, *Peptide Based Drug Design*, ACS, Washington (1995)).

As used herein, the term "amino acid" refers to one of the twenty naturally occurring amino acids, including, unless stated otherwise, L-amino acids and D-amino acids. The term amino acid also refers to compounds such as chemically modified amino acids including amino acid analogs, naturally occurring amino acids that are not usually incorporated into proteins such as norleucine, and chemically synthesized compounds having properties known in the art to be characteristic of an amino acid, provided that the compound can be substituted within a peptide such that it retains reactivity with Crohn's disease sera or tolerogenic activity. Examples of amino acids and amino acids analogs are listed in Gross and Meienhofer, *The Peptides: Analysis, Synthesis, Biology*, Academic Press, Inc., New York (1983). An amino acid also can be an amino acid mimetic, which is a structure that exhibits substantially the same spatial arrangement of functional groups as an amino acid but does not necessarily have both the α-amino and α-carboxyl groups characteristic of an amino acid.

A reactive or tolerogenic fragment of an OmpC antigen useful in the invention can be produced or synthesized using methods well known in the art. Such methods include recombinant DNA methods and chemical synthesis methods for production of a peptide. Recombinant methods of producing a peptide through expression of a nucleic acid sequence encoding the peptide in a suitable host cell are well known in the art and are described, for example, in Ausubel et al., supra, 1999.

A reactive or tolerogenic fragment of an OmpC antigen useful in the invention also can be produced by chemical synthesis, for example, by the solid phase peptide synthesis method of Merrifield et al., *J. Am. Chem. Soc.* 85:2149 (1964). Standard solution methods well known in the art also can be used to synthesize a reactive or tolerogenic fragment useful in the invention (see, for example, Bodanszky, *Principles of Peptide Synthesis*, Springer-Verlag, Berlin (1984) and Bodanszky, *Peptide Chemistry*, Springer-Verlag, Berlin (1993)). A newly synthesized peptide can be purified, for example, by high performance liquid chromatography (HPLC), and can be characterized using, for example, mass spectrometry or amino acid sequence analysis.

It is understood that limited modifications can be made to an OmpC antigen without destroying its biological function. Similarly, limited modifications can be made to a reactive fragment of an OmpC antigen or a tolerogenic fragment of this antigen without destroying its reactivity or tolerogenic activity. A modification of an antigen disclosed herein that does not destroy its preferential reactivity with IgA antibodies in the sera of patients having Crohn's disease or a modification of an antigen disclosed herein that does not destroy tolerogenic activity is within the definition of an OmpC antigen. Similarly, a modification of a reactive fragment of an antigen disclosed herein that does not destroy its ability to form a complex with IgA antibodies in the sera of a patient having Crohn's disease is within the definition of a reactive fragment. Furthermore, a modification of a tolerogenic fragment of an OmpC antigen that does not destroy its ability to produce a decreased immunological response is within the definition of a tolerogenic fragment of an OmpC antigen. A modification can be, for example, an addition, deletion, or substitution of amino acid residues; substitution of a compound that mimics amino acid structure or function; or addition of chemical moieties such as amino or acetyl groups. The activity of a modified OmpC antigen or a modified fragment of an OmpC antigen can be assayed, for example, using one of the assays for reactivity or tolerogenic activity disclosed herein.

A particularly useful modification confers increased stability. Incorporation of one or more D-amino acids is a modification useful in increasing stability of a OmpC antigen or fragment thereof. Similarly, deletion or substitution of lysine can increase stability by protecting against degradation. For example, such a substitution can increase stability and, thus, bioavailability of an OmpC antigen or a tolerogenic fragment thereof, provided that the substitution does not significantly impair reactivity or tolerogenic activity.

The invention further provides a method of diagnosing Crohn's disease by determining the presence or absence of IgA anti-OmpC antibodies in the subject and the presence or absence of IgA anti-*Saccharomyces cerevisiae* antibodies (ASCA) in the subject, where the presence of IgA anti-OmpC antibodies or the presence of IgA ASCA in the subject each independently indicates that the subject has Crohn's disease. The presence of IgA ASCA can be determined, for example, by reactivity with purified yeast cell wall phosphopeptidomannan (PPM), which can be prepared, for example, from ATCC strain #38926. Methods for determining the presence of IgA ASCA are exemplified herein in Example III. As used herein, the "presence of IgA ASCA" means IgA reactivity against *S. cerevisiae* that is greater than 20% of the reactivity given by reference (known positive) Crohn's disease sera.

Anti-*Saccharomyces cerevisiae* antibodies (ASCA) are characteristically elevated in patients having Crohn's disease although the nature of the *S. cerevisiae* antigen supporting the specific antibody response in CD is unknown (Sendid et al., *Clin. Diag. Lab. Immunol.*, 3:219-226 (1996)). These antibodies may represent a response against yeasts present in common food or drink or a response against yeasts that colonize the gastrointestinal tract. Studies with periodate oxidation have shown that the epitopes recognized by ASCA in CD patient sera contain polysaccharides. Oligomannosidic epitopes are shared by a variety of organisms including different yeast strains and genera, filamentous fungi, viruses, bacteria and human glycoproteins. Thus, the mannose-induced antibody responses in CD may represent a response against a pathogenic yeast organism or may represent a response against a cross-reactive oligomannosidic epitope present, for example, on a human glycoprotein autoantigen. Regardless of the nature of the antigen, elevated levels of serum ASCA are a differential marker for Crohn's disease, with only low levels of ASCA reported in UC patients (Sendid et al., supra, 1996).

IgA ASCA can be detected using an antigen specific for ASCA, which is any antigen or mixture of antigens that is bound specifically by ASCA. Although ASCA antibodies were initially characterized by their ability to bind *S. cerevisiae*, those of skill in the art will understand that an antigen specific for ASCA can be obtained from *S. cerevisiae*, or can be obtained from a variety of other sources so long as the antigen is capable of binding specifically to ASCA-antibodies. Accordingly, exemplary sources of an antigen specific for ASCA contemplated for use in the methods of the invention include whole killed yeast cells, such as from the genera *Saccharomyces* and *Candida*, yeast cell wall phosphopeptidomannan (PPM), oligomannosides, neoglycolipids, anti-ASCA idiotypic antibodies, and the like. As described above, different species and strains of yeast, including *Saccharomyces*, can be used as an antigen specific for ASCA in the methods provided herein. For example, *S. cerevisiae* strain Su1, Su2, CBS 1315 or BM 156, or *Candida albicans* strain VW32, can be used as an antigen specific for ASCA in the methods of the invention.

Preparations of yeast cell wall mannans, or phosphopeptidomannans (PPM), are also contemplated herein as antigens specific for ASCA. These water soluble surface antigens can be prepared by appropriate extraction techniques, including autoclaving as described in Example III or can be obtained commercially (see Lindberg et al., *Gut* 33:909-913 (1992)). The acid stable fraction of yeast cell wall PPM also can be useful in the methods of the invention (Sendid et al., supra, 1996). An exemplary PPM for use in diagnosing clinical subtypes of Crohn's disease is derived from *S. cerevisiae* strain ATCC #38926.

Purified oligosaccharide antigens, such as oligomannosides specific for ASCA, also are contemplated for use in the methods of the invention. For use herein, the purified oligomannoside antigens are preferably converted into neoglycolipids as described in Faille et al., *Eur. J. Microbiol. Infect. Dis.* 11:438-446 (1992). One skilled in the art understands that the reactivity of such an oligomannoside antigen with ASCA can be optimized by varying the mannosyl chain length (Frosh et al., *Proc. Natl. Cad. Sci. USA*, 82:1194-1198 (1985)); the anomeric configuration (Fukazawa et al., *In E. Kurstak* (ed.), *Immunology of Fungal Disease*, Marcel Dekker Inc., New York, pp. 37-62 (1989); Nishikawa et al, *Microbiol. Immunol.*, 34:825-840 (1990); Poulain et al., *Eur. J. Clin. Microbiol*, 23:46-52 (1993); Shibata et al., *Arch. Biochem. Biophys.*, 243:338-348 (1985); and Trinel et al., *Infect. Immun.*, 60:3845-3851 (1992)); or the position of the linkage (Kikuchi et al., *Planta*, 190:525-535 (1993)).

An oligomannoside antigen specific for ASCA can include the mannotetraose Man(1→3)Man(1→2)Man(1→2)Man, and can be purified from PMM as described in Faille et al., supra, 1992. An exemplary neoglycolipid for use in the methods of the invention can be constructed by releasing the oligomannoside from its respective PPM and subsequently coupling the released oligomannoside to 4-hexadecylaniline or the like.

The invention additionally provides a method of diagnosing Crohn's disease by determining the presence or absence of IgA anti-OmpC antibodies in the subject and the presence or absence of IgA anti-I-2 polypeptide antibodies in the subject, where the presence of IgA anti-OmpC antibodies or the presence of IgA anti-I-2 polypeptide antibodies in the subject each independently indicates that the subject has Crohn's disease. In one embodiment, the presence of IgA anti-I-2 polypeptide antibodies is determined by IgA reactivity against an I-2 polypeptide having substantially the amino acid sequence of SEQ ID NO: 3.

The methods of the invention relate to determining the presence or absence of IgA anti-I-2 polypeptide antibodies in a subject. As used herein, the "presence of IgA anti-I-2 polypeptide antibodies" or "IgA anti-I-2 antibodies" means IgA reactivity against an I-2 polypeptide that is greater than two standard deviations above the IgA anti-I-2 mean reactivity of control (normal) sera analyzed under the same conditions.

As used herein, the term "I-2 polypeptide" means a polypeptide having substantially the same amino acid sequence as the microbial I-2 polypeptide (SEQ ID NO: 3) shown in FIG. 6. The microbial I-2 polypeptide (SEQ ID NO: 3) is a polypeptide of 100 amino acids sharing some similarity to bacterial transcriptional regulators, with the greatest similarity in the amino-terminal 30 amino acids. The I-2 encoding nucleic acid (SEQ ID NO: 2) is differentially present in involved Crohn's disease tissue, as compared to mucosa macroscopically free of disease. An I-2 polypeptide, or reactive fragment thereof, can be prepared, for example, using recombinant methods as set forth in Example IV.

An I-2 polypeptide having substantially the same amino acid sequence as SEQ ID NO: 3 can be the naturally occurring I-2 polypeptide (SEQ ID NO: 3) or a related polypeptide having substantial amino acid sequence similarity to this sequence. Such related polypeptides include isotype variants or homologs of the amino acid sequence shown in FIG. 6. As used herein, the term I-2 polypeptide generally describes polypeptides generally having an amino acid sequence with greater than about 50% identity, preferably greater than about 60% identity, more preferably greater than about 70% identity, and can be a polypeptide having greater than about 80%, 90%, 95%, 97%, or 99% amino acid sequence identity with SEQ ID NO: 3, said amino acid identity determined with CLUSTALW using the BLOSUM 62 matrix with default parameters.

Further provided by the invention is a method of diagnosing Crohn's disease in a subject by determining the presence or absence of IgA anti-OmpC antibodies in the subject; determining the presence or absence of IgA ASCA in the subject; and determining the presence or absence of IgA anti-I-2 polypeptide antibodies in the subject, where the presence of the IgA anti-OmpC antibodies, the presence of IgA ASCA or the presence of IgA anti-I-2 polypeptide antibodies each independently indicates that the subject has Crohn's disease.

Previous studies have shown ANCA reactivity in a small portion of patients with Crohn's disease, although these antibodies are elevated more frequently in patients with ulcerative colitis. The reported prevalence in CD varies from 0 to 43% with most studies reporting that 10 to 30% of CD patients express ANCA (see, for example, Saxon et al., *J. Allergy Clin. Immunol.* 86:202-210 (1990); Cambridge et al., *Gut* 33:668-674 (1992); Pool et al., *Gut* 3446-50 (1993); and Brokroelofs et al., *Dig. Dis. Sci.* 39:545-549 (1994).

In a method of the invention, the presence or absence of pANCA can be optionally determined in the subject, for example, by reactivity with fixed neutrophil. As used herein, the term "perinuclear anti-neutrophil cytoplasmic antibody" is synonymous with "pANCA" and refers to an antibody that reacts specifically with a neutrophil to give perinuclear to nuclear staining or cytoplasmic staining with perinuclear highlighting. A method for determining the presence of pANCA in a subject is exemplified herein in Example V.

The invention further provides a method of inducing tolerance in a patient with Crohn's disease by administering an effective dose of an OmpC antigen, or tolerogenic fragment thereof, to the patient with Crohn's disease. An OmpC antigen useful in a method of inducing tolerance can include, for example, the sequence SEQ ID NO: 1.

As used herein, the term "effective dose" means the amount of an OmpC antigen, or a tolerogenic fragment thereof, useful for inducing tolerance in a patient having Crohn's disease. For induction of oral tolerance, for example, multiple smaller oral doses can be administered or a large dose can be administered. Such doses can be extrapolated, for example, from the induction of tolerance in animal models (see, for example, Trentham et al., *Science* 261:1727-1730 (1993)).

Various molecules are known in the art to cause, promote or enhance tolerance, and an OmpC antigen or tolerogenic fragment thereof can be combined, if desired, with a tolerogizing molecule. See, for example, U.S. Pat. No. 5,268,454, and citations therein, each of which is incorporated herein by reference. As used herein, the term "tolerogizing molecule" means a molecule, compound or polymer that causes, promotes or enhances tolerogenic activity when combined with an OmpC antigen or fragment thereof. A tolerogizing molecule can be optionally conjugated to an OmpC antigen and can be, for example, polyethylene glycol. Such molecules are well known in the art (see, for example, U.S. Pat. No. 5,268,454, supra).

An effective dose of an OmpC antigen, or a fragment thereof, for inducing tolerance can be administered by methods well known in the art. Oral tolerance is well-recognized in the art as a method of treating autoimmune disease (see, for example, Weiner, *Hospital Practice*, pp. 53-58 (Sep. 15, 1995)). For example, orally administered autoantigens suppress several experimental autoimmune models in a disease- and antigen-specific fashion; the diseases include experimental autoimmune encephalomyelitis, uveitis, and myasthenia, collagen- and adjuvant-induced arthritis, and diabetes in the NOD mouse (see, for example, Weiner et al., *Ann. Rev. Immunol.* 12:809-837 (1994)). Furthermore, clinical trials of oral tolerance have produced positive results in treating multiple sclerosis, rheumatoid arthritis and uveitis. Modes of administration include parenteral administration and subcutaneous injection (Johnson, *Ann. Neurology* 36(suppl.):S115-S117 (1994)).

The term "tolerogenic fragment," as used in reference to an OmpC antigen, means a peptide or polypeptide portion of the antigen that has tolerogenic activity as defined by its ability either alone, or in combination with another molecule, to produce a decreased immunological response. Thus, a tolerogenic fragment of an OmpC antigen is a peptide or polypeptide that has substantially the same amino acid sequence as a portion of SEQ ID NO: 1 and tolerogenic activity as defined by its ability either alone, or in combination with another molecule, to produce a decreased immunological response. A tolerogenic fragment of an OmpC antigen can have from about three amino acids to about 90 amino acids. A tolerogenic fragment of an OmpC antigen can have, for example, at least 5, 8, 10, 12, 15, 18, 20 or 25 amino acids. For example, a tolerogenic fragment of an OmpC antigen can have from five to fifty amino acids, from eight to fifty amino acids, or from ten to fifty amino acids. More preferably, a tolerogenic fragment has from eight to twenty amino acids or from ten to twenty amino acids. Most preferably, a tolerogenic fragment has from twelve to twenty amino acids or from fifteen to twenty amino acids.

A tolerogenic fragment of an OmpC antigen can be identified using one of a variety of assays, including in vitro assays such as T-cell proliferation or cytokine secretion assays and in vivo assays such as the induction of tolerance in murine models of inflammatory bowel disease. T-cell proliferation assays, for example, are well recognized in the art as predictive of tolerogenic activity (see, for example, Miyahara et al., *Immunol.* 86:110-115 (1995) or Lundin et al, *J. Exp. Med.* 178:187-196 (1993)). A T-cell proliferation assay can be performed by culturing T-cells with irradiated antigen-presenting cells, such as normal spleen cells, in microtiter wells for 3 days with varying concentrations of the fragment to be assayed; adding $^3$H-thymidine; and measuring incorporation of $^3$H-thymidine into DNA. In such an assay, a fragment of an OmpC antigen can be tested for activity, for example, at concentrations of 20 µg/ml and 40 µg/ml.

A tolerogenic fragment of an OmpC antigen can be identified using a T-cell cytokine secretion assay known in the art. For example, T cells can be cultured with irradiated antigen-presenting cells in microtiter wells with varying concentrations of the fragment of interest and, after three days, the culture supernatants can be assayed for IL-2, IL-4 or IFN-γ as described in Czerinsky et al., *Immunol. Rev.* 119:5-22 (1991).

Primary T-cells for use in a T-cell proliferation assay or cytokine secretion assay, for example, can be isolated from lamina propria or peripheral blood. In addition, a convenient source of T-cells for use in an in vitro assay for tolerogenic activity can be a T-cell line established from an IBD patient such as a Crohn's disease patient, from a murine model of IBD or from a healthy animal immunized with an OmpC antigen of the invention. A preferred source of T-cells for use in identifying a tolerogenic fragment of an OmpC antigen is a Crohn's disease patient.

A T-cell line can be established from a patient with CD or UC, for example, by culturing T lymphocytes with about 1 µg/ml recombinant OmpC antigen or OmpC fusion protein, in the presence of low concentrations of growth-supporting IL-2 (about 10 µg/ml). A T-cell line can be established by culturing T lymphocytes with antigen-presenting cells and feeding the cells on an alternating four to five day cycle with either IL-2 and an OmpC antigen, or IL-2 alone, as described in Nanda et al., *J. Exp. Med.* 176:297-302 (1992). A cell line that develops into a reliably proliferating cell line dependent on the presence of an OmpC antigen is particularly useful in identifying tolerogenic fragments. The establishment of T-cell lines from small intestinal mucosa is described, for example, in Lundin et al., supra, 1993. T cell lines dependent upon the presence of an OmpC antigen and useful for identifying tolerogenic fragments of an OmpC antigen can be prepared similarly.

A tolerogenic fragment also can be identified by its ability to induce tolerance in vivo, as indicated by a decreased immunological response, which can be a decreased T-cell response, such as a decreased proliferative response or cytokine secretion response as described above, or a decreased antibody titer to the antigen. A neonatal or adult mouse can be tolerized with a fragment of an OmpC antigen, and a T-cell response or anti-OmpC antibody titer can be assayed after challenging by immunization. For example, a neonatal mouse can be tolerized within 48 hours of birth by intraperitoneal administration of about 100 µg of a fragment of an OmpC antigen emulsified with incomplete Freund's adjuvant and subsequently immunized with I-2 polypeptide at about 8 weeks of age (see, for example, Miyahara, supra, 1995). An adult mouse can be tolerized intravenously with about 0.33 mg of a fragment of an OmpC antigen, administered daily for three days (total dose 1 mg), and immunized one week later with an OmpC antigen. A decreased T-cell response, such as decreased proliferation or cytokine secretion, which indicates tolerogenic activity, can be measured using T-cells harvested 10 days after immunization. In addition, a decreased anti-OmpC antibody titer, which also indicates tolerogenic activity, can be assayed using blood harvested 4-8 weeks after immunization. Methods for assaying a T-cell response or anti-OmpC antigen antibody titer are described above and are well known in the art.

A tolerogenic fragment of an OmpC antigen also can be identified using a murine model of inflammatory bowel disease. Neonatal or adult mice having IBD-like disease can be tolerized with a fragment of an OmpC antigen as described above, and the T-cell response or anti-OmpC antibody titer assayed. A decreased T-cell response or decreased antibody titer to the antigen indicates a decreased immunological response and, thus, serves to identify a tolerogenic fragment of an OmpC antigen. In addition, a tolerogenic fragment of an OmpC antigen can be identified by the ability to reduce the frequency, time of onset or severity of colitis in a murine model of IBD.

Several well-accepted murine models of inflammatory bowel disease can be useful in identifying a tolerogenic fragment of an OmpC antigen. For example, mice with targeted disruption of the gene encoding the alpha subunit of the G-protein Gi2, is a well known model exhibiting features of human bowel disease (Hornquist et al., *J. Immunol.* 158:

1068-1077 (1997); Rudolph et al., *Nat. Genet.* 10:143-150 (1995)). Mice deficient in IL-10 as described in Kuhn et al., *Cell* 75:263-274 (1993), and mice deficient in IL-2 as described in Sadlack et al., *Cell* 75:253-261 (1993), also have colitis-like disease and are useful in identifying a tolerogenic fragment of an OmpC antigen. Furthermore, mice with mutations in T cell receptor (TCR) α, TCR β, TCR β×δ, or the class II major histocompatiblility complex (MHC) as described in Mombaerts et al., *Cell* 75:275-282 (1993), develop inflammatory bowel disease and, thus, are useful in identifying a tolerogenic fragment of an OmpC antigen. Similarly, a fragment can be assayed for tolerogenic activity in a SCID mouse reconstituted with CD45RB CD4+ T-cells, which is a well-accepted model of inflammatory bowel disease, as described in Powrie et al., *Immunity* 1:553-562 (1994). Additional animal models of IBD also are well known in the art (see, for example, Podolsky, *Acta Gastroenterol. Belg.* 60:163-165 (1997); and Bregenholt et al., *APMIS* 105: 655-662 (1997)). Thus, a tolerogenic fragment of an OmpC antigen can be readily identified by an in vitro or in vivo assay disclosed herein or by another assay well known in the art.

A reactive or tolerogenic fragment of an OmpC antigen can be identified by screening a large collection, or library, of peptides of interest or random peptides for reactivity or tolerogenic activity. For example, a panel of peptides spanning the entire sequence of an OmpC antigen can be screened for reactivity or tolerogenic activity as described above. Such a panel can be a panel of 15-mer peptides spanning the sequence of the OmpC antigen (SEQ ID NO: 1), each overlapping by three or five residue shifts using the Mimotope cleavable pin technology (Cambridge Research Biochemicals, Wilmington, Del.), as described by Geysen et al., *Science* 235:1184 (1987). The panel is subsequently screened for reactivity or tolerogenic activity using one of the assays described above (see, for example, Miyahara et al., supra, 1995). A library of peptides to be screened also can be a population of peptides related in amino acid sequence to SEQ ID NO: 1 but having one or more amino acids that differ from SEQ ID NO: 1.

Additional peptides to be screened include, for example, tagged chemical libraries of peptides and peptidomimetic molecules. Peptide libraries also comprise those generated by phage display technology. Phage display technology includes the expression of peptide molecules on the surface of phage as well as other methodologies by which a protein ligand is or can be associated with the nucleic acid which encodes it. Methods for production of phage display libraries, including vectors and methods of diversifying the population of peptides which are expressed, are well known in the art (see, for example, Smith and Scott, *Methods Enzymol.* 217:228-257 (1993); Scott and Smith, *Science* 249:386-390 (1990); and Huse, WO 91/07141 and WO 91/07149). These or other well known methods can be used to produce a phage display library which can be screened, for example, with one of the disclosed assays for reactivity or tolerogenic activity. If desired, a population of peptides can be assayed for activity en masse. For example, to identify a reactive fragment of an OmpC antigen, a population of peptides can be assayed for the ability to form a complex with patient sera containing IgA anti-OmpC antigen reactivity; the active population can be subdivided, and the assay repeated in order to isolate the reactive fragment from the population.

A reactive or tolerogenic fragment of an OmpC antigen also can be identified by screening, for example, fragments of the polypeptide produced by chemical or proteolytic cleavage. Methods for chemical and proteolytic cleavage and for purification of the resultant protein fragments are well known in the art (see, for example, Deutscher, *Methods in Enzymology*, Vol. 182, "Guide to Protein Purification," San Diego: Academic Press, Inc. (1990)). For example, a chemical such as cyanogen bromide or a protease such as trypsin, chymotrypsin, V8 protease, endoproteinase Lys-C, endoproteinase Arg-C or endoproteinase Asp-N can be used to produce convenient fragments of an OmpC antigen that can be screened for reactivity or tolerogenic activity using one of the assays disclosed herein.

The following examples are intended to illustrate but not limit the present invention.

EXAMPLE I

Purification of OmpC

This example describes purification of OmpC using spheroplast lysis.

OmpF-/-/OmpA-/- mutant *E. coli* were inoculated from a glycerol stock into 10-20 ml of Luria Bertani broth supplemented with 100 µg/ml streptomycin (LB-Strep), and cultured vigorously at 37° C. for ~8 hours to log phase. This starter culture was used to inoculate one liter of LB-strep media, and the 1 L culture grown for less than 15 hours.

The cells were harvested by centrifugation (JS-4.2, 4K/15 min/4° C.). If necessary, cells were washed twice with 100 ml of ice cold 20 mM Tris-Cl pH 7.5. The cells were subsequently resuspended in ice cold spheroplast forming buffer (20 mM Tris-Cl pH 7.5, 20% sucrose, 0.1 M EDTA pH 8.0, 1 mg/ml lysozyme), after which the resuspended cells were incubated on ice for 20 minutes to 2 hours with occasional mixing by inversion.

If required, the spheroplasts were centrifuged (JA-17, 5.5 k/10 min/4° C.) and resuspended in a smaller volume of spheroplast forming buffer (SFB). The spheroplast pellet was optionally frozen prior to resuspension in order to improve lysis efficiency. Hypotonic buffer was avoided in order to avoid bursting the spheroplasts and releasing chromosomal DNA, which significantly decreases the efficiency of lysis.

The spheroplast preparation was diluted 14-fold into ice cold 10 mM Tris-Cl pH 7.5, 1 mg/ml DNase-I, and vortexed vigorously. The preparation was sonicated on ice 4×30 seconds at 50% power at setting 4, with a pulse "On time" of 1 second, without foaming or overheating the sample.

Cell debris was pelleted by centrifugation (JA-17, 5-10K/10 min/4° C.), and the supernatant removed and clarified by centrifugation a second time (10K/10 min/4° C.). The supernatant was removed without collecting any part of the pellet, and placed into ultra centrifuge tubes. The tubes were filled to 1.5 millimeter from top with 20 mM Tris-Cl pH 7.5.

The membrane preparation was pelleted by ultra centrifugation at 100,000 g (35K/1 hour/4° C. in Beckman SW 60 swing bucket rotor). The pellet was resuspended by homogenizing into 20 mM Tris-Cl pH 7.5 using a 1 ml blue pipette tip and squirting the pellet closely before pipetting up and down for approximately ~10 minutes per tube.

In a 15 ml screw cap tube filled with 4 mls, the material was extracted for 1 hour in 20 mM Tris-Cl pH 7.5 with 1% SDS, with rotation at 37° C. The preparation was transferred to ultra centrifugation tubes, and the membrane pelleted at 100,000 g (35K/1 hour/4° C. in Beckman SW 60). The pellet was resuspended by homogenizing into 20 mM Tris-Cl pH 7.5 as before. The membrane preparation was optionally left at 4° C. overnight.

OmpC was extracted for 1 hour with rotation at 37° C. in 20 mM Tris-Cl pH 7.5, 3% SDS, and 0.5 M NaCl (SDS will precipitate if kept below 37° C.). The material was transferred to ultra centrifugation tubes, and the membrane pelleted by centrifugation at 100,000 g (35K/1 hour/30° C. in Beckman SW 60). Lower temperatures were avoided since further cooling will result in extracted protein salting out of solution.

The supernatant containing extracted OmpC was then dialyzed against more than 10,000 volumes to eliminate high salt content. SDS was removed by detergent exchange against 0.2% Triton. Triton was removed by further dialysis against 50 mM Tris-Cl.

Purified OmpC, which functions as a porin in its trimeric form, is characterized as follows when analyzed by SDS-PAGE. Electrophoresis at room temperature resulted in a ladder of ~100 kDa, ~70 kDa, and ~30 kDa bands. Heating for 10-15 minutes at 65-70° C. partially dissociated the complex and resulted in only dimers and monomers (~70 kDa and ~30 kDa bands). Boiling for 5 minutes resulted in monomers of 38 kDa.

EXAMPLE II

ANTI-IgA OmpC ELISA Assays

This example describes an ELISA assay for direct detection of IgA anti-OmpC antibodies in patient sera.

The OmpC direct ELISA assay was performed as follows. Plates (Immulon 3, DYNEX Technologies, Chantilly, Va.) were coated overnight at 4 C with 100 µl/well of OmpC prepared as described above at 0.25 µg/ml in borate buffered saline, pH 8.5. After three washes in 0.05% Tween 20 in phosphate buffered saline (PBS), the plates were blocked with 150 µl/well of 0.5% bovine serum albumin in PBS, pH 7.4 (BSA-PBS) for 30 minutes at room temperature (RT). The blocking solution was then discarded, and 100 µl/well of serum from Crohn's disease patients, ulcerative colitis patients and normal controls diluted 1:100 was added and incubated for 2 hours at room temperature. After washing the plates as before, alkaline phosphatase-conjugated indicator antibody (goat anti-human IgA (α-chain specific) from Jackson ImmunoResearch, West Grove, Pa.) was added to the plates at a dilution of 1:1000 in BSA-PBS, and the plates were incubated at room temperature for 2 hours. The plates were subsequently washed three times with 0.05% Tween 20 in phosphate buffered saline, followed by another three washes with Tris buffered normal saline, pH 7.5. Substrate solution (1.5 mg/ml disodium P-nitrophenol phosphate (Amresco; Solon, Ohio), 2.5 mM $MgCl_2$, 0.01 M Tris, pH 8.6) was added at 100 µl/well, and color was allowed to develop for one hour before the plates were read at 405 nm.

IgA OmpC positive reactivity was defined as reactivity greater than two standard deviations above the mean reactivity obtained with control (normal) sera analyzed at the same time as the test samples.

EXAMPLE III

IgA ASCA ELISA Assay

This example demonstrates that the presence of IgA anti-*Saccharomyces cerevisiae* antibodies in patient sera can be determined using an ELISA microplate assay.

A. Preparation of Yeast Cell Wall Mannan

Yeast cell wall mannan was prepared as follows and as described in Faille et al. *Eur. J. Clin. Microbiol. Infect. Dis.* 11:438-446 (1992) and in Kocourek and Ballou et al., *J. Bacteriol* 100:1175-1181 (1969). A lyophilized pellet of yeast *Saccharomyces uvarum* was obtained from the American Type Culture Collection (#38926). Yeast were reconstituted in 10 ml 2×YT medium, prepared according to Sambrook et al., *Molecular Cloning* Cold Spring Harbor Laboratory Press (1989). *S. uvarum* were grown for two to three days at 30° C. The terminal *S. uvarum* culture was inoculated on a 2×YT agar plate and subsequently grown for two to three days at 30° C. A single colony was used to inoculate 500 ml 2×YT media, and grown for two to three days at 30° C. Fermentation media (pH 4.5) was prepared by adding 20 gm glucose, 2 gm bacto-yeast extract, 0.25 gm $MgSO_4$ and 2.0 ml 28% $H_3PO_4$ per liter distilled water. The 500 ml culture was used to inoculate 50 liters of fermentation media, and the culture fermented for three to four days at 37° C.

*S. uvarum* mannan extract was prepared by adding 50 ml 0.02 M citrate buffer (5.88 gm/l sodium citrate; pH 7.0+/−0.1) to each 100 grams of cell paste. The cell/citrate mixture was autoclaved at 125° C. for ninety minutes and allowed to cool. After centrifuging at 5000 rpm for 10 minutes, the supernatant was removed and retained. The cells were then washed with 75 ml 0.02 M citrate buffer and the cell/citrate mixture again autoclaved at 125° C. for ninety minutes. The cell/citrate mixture was centrifuged at 5000 rpm for 10 minutes, and the supernatant retained.

In order to precipitate copper/mannan complexes, an equal volume of Fehling's Solution was added to the combined supernatants while stirring. The complete Fehling's solution was prepared by mixing Fehling's Solution A with Fehling's Solution B in a 1:1 ratio just prior to use. The copper complexes were allowed to settle, and the liquid decanted gently from the precipitate. The copper/mannan precipitate complexes were then dissolved in 6-8 ml 3N HCl per 100 grams yeast paste.

The resulting solution was poured with vigorous stirring into 100 ml of 8:1 methanol:acetic acid, and the precipitate allowed to settle for several hours. The supernatant was decanted and discarded; then the wash procedure was repeated until the supernatant was colorless, approximately two to three times. The precipitate was collected on a scintered glass funnel, washed with methanol and air dried overnight. On some occasions, the precipitate was collected by centrifugation at 5000 rpm for 10 minutes before washing with methanol and air drying overnight. The dried mannan powder was dissolved in distilled waster, using approximately 5 ml water per gram of dry mannan powder. The final concentration of *S. uvarum* cell wall mannan was approximately 30 µg/ml.

B. Preparation of *S. uvarum* mannan ELISA Plates

*S. uvarum* cell mannan ELISA plates were saturated with antigen as follows. Purified *S. uvarum* mannan prepared as described above was diluted to a concentration of 100 µg/ml with phosphate buffered saline/0.2% sodium azide (PBS-N3). Using a multi-channel pipettor, 100 µl of 100 µg/ml *S. uvarum* mannan was added per well of a Costar 96-well hi-binding plate (catalogue number 3590; Costar Corp., Cambridge, Mass.). The antigen was allowed to coat the plate at 4° C. for a minimum of 12 hours. Each lot of plates was compared to a previous lot before use. Plates were stored at 2-8° C. for up to one month.

C. Analysis of Patient Sera

Patient sera were analyzed in duplicate for anti-IgG or anti-IgA reactivity. Microtiter plates saturated with antigen as described above were incubated with phosphate buffered saline/0.05% Tween-20 for 45 minutes at room temperature to inhibit nonspecific antibody binding. Patient sera were subsequently added at a dilution of 1:80 for IgA and incubated for 1 hour at room temperature. Wells were washed three times with PBS/0.05% Tween-20. Then a 1:1000 dilution of alkaline phosphatase-conjugated goat anti-human IgA (Jackson Immunoresearch, Westgrove, Pa.) was added, and the microtiter plates incubated for 1 hour at room temperature. A solution of p-nitrophenol phosphate in diethanolamine substrate buffer was added, and color development allowed to proceed for 10 minutes. Absorbance at 405 nm was analyzed using an automated EMAX plate reader (Molecular Devices, Sunnyvale, Calif.).

Standard binding of pooled sera from patients with an established diagnosis of Crohn's disease was used as a standard reference for binding and set to be 100 ELISA units. Results with test patient sera were expressed as a percentage of the standard binding of the reference CD sera. ASCA-positively was defined as IgA ASCA reactivity that was greater than 20% of the reference CD sera.

EXAMPLE IV

IgA I-2 ELISA

This example demonstrates that the I-2 polypeptide can be determined using ELISA analysis.

A. GST-I-2 Fusion Protein

The full-length I-2 encoding nucleic acid sequence (SEQ ID NO: 3) was cloned into the GST expression vector pGEX. After expression in *E. coli*, the protein was purified on a GST column. The purified protein was shown to be of the expected molecular weight by silver staining, and had anti-GST reactivity upon western analysis.

B. ELISA Analysis

Human IgA antibodies that bind the I-2 polypeptide (SEQ ID NO: 3) were detected by direct ELISA assays essentially as follows. Plates (Immulon 3; DYNEX Technologies; Chantilly, Va.) were coated overnight at 4° C. with 100 µl/well GST-I-2 fusion polypeptide (5 µg/ml in borate buffered saline, pH 8.5). After three washes in 0.05% Tween 20 in phosphate buffered saline (PBS), the plates were blocked with 150 µl/well of 0.5% bovine serum albumin in PBS, pH 7.4 (BSA-PBS) for 30 minutes at room temperature. The blocking solution was then replaced with 100 µl/well of Crohn's disease or normal control serum, diluted 1:100. The plates were then incubated for 2 hours at room temperature and washed as before. Alkaline phosphatase conjugated secondary antibody [goat anti-human IgA (α-chain specific), Jackson ImmunoResearch, West Grove, Pa.] was added to the IgA plates at a dilution of 1:1000 in BSA-PBS. The plates were incubated for 2 hours at room temperature before washing three times with 0.05% Tween 20/PBS followed by another three washes with Tris buffered normal saline, pH 7.5. Substrate solution (1.5 mg/ml disodium P-nitrophenol phosphate (Aresco; Solon, Ohio) in 2.5 mM $MgCl_2$, 0.01 M Tris, pH 8.6) was added at 100 µl/well, and color allowed to develop for one hour. The plates were then analyzed at 405 nm.

IgA I-2 positive reactivity was defined as reactivity greater than two standard deviations above the mean reactivity obtained with control (normal) sera analyzed at the same time as the test samples.

EXAMPLE V

ELISA and Indirect Immunofluorescence for Determining pANCA Status

This example describes methods for determining the pANCA status of a subject.

A. Presence of ANCA was Determined by Fixed Neutrophil ELISA

A fixed neutrophil enzyme-linked immunosorbent assay was used to detect ANCA as described in Saxon et al., *J. Allergy Clin. Immunol.* 86:202-210 (1990), and all samples were analyzed in a blinded fashion. Microtiter plates were coated with $2.5 \times 10^5$ neutrophils per well and treated with 100% methanol to fix the cells. Cells were incubated with 0.25% bovine serum albumin (BSA) in phosphate-buffered saline to block nonspecific antibody binding. Next, control and coded sera were added at a 1:100 dilution to the bovine serum/phosphate-buffered saline blocking buffer. Alkaline phosphatase conjugated goat F(ab')$_2$ anti-human immunoglobulin G (γ-chain specific) antibody (Jackson Immunoresearch Labs, Inc., West Grove, Pa.) was added at a 1:1000 dilution to label neutrophil bound antibody. A p-nitrophenol phosphate substrate solution was added and color development was allowed to proceed until absorbance at 405 nm in the positive control wells was 0.8-1.0 optical density units greater than the absorbance in blank wells.

B. Indirect Immunofluorescence Assay for Determination of ANCA Staining Pattern

Indirect immunofluorescent staining was performed on samples that were ANCA-positive by ELISA to determine whether the predominant staining pattern was perinuclear (pANCA) or cytoplasmic (cANCA). Glass slides containing approximately 100,000 neutrophils per slide were prepared by cytocentrifugation (Shandon Cytospin, Cheshire, England) and they were fixed in 100% methanol, air-dried, and stored at −20° C. The fixed neutrophils were incubated with human sera were diluted (1:20), and the reaction was visualized with fluorescein-labeled F(ab')$_2$ γ chain-specific antibody as described in Saxon et al., supra, 1990. The slides were examined using an epifluorescence-equipped Olympus BH-2 microscope (Olympus, Lake Success, N.Y.).

pANCA positivity was defined as a perinuclear staining pattern combined with ELISA reactivity greater than two standard deviations above the mean reactivity obtained with control (normal) sera analyzed at the same time as the test samples.

All journal article, reference, and patent citations provided above, in parentheses or otherwise, whether previously stated or note, are incorporated herein by reference.

Although the invention has been described with reference to the examples above, it should be understood that various modifications can be made without departing from the spirit of the invention. Accordingly, the invention is limited only by the following claims.

What is claimed:

1. An assay system to aid in the detection of Crohn's disease, said assay system comprising:

(a) a plate comprising an OmpC antigen, or reactive fragment thereof, wherein said OmpC antigen comprises the amino acid sequence of SEQ ID NO:1 or 90% identity thereof;

(b) an indicator secondary antibody specific for an OmpC autoantibody; and (c) instructions that specifically detect for Crohn's Disease by detecting for the presence of a complex of said OmpC antigen in (a), said OmpC autoantibody, and said indicator secondary antibody that specifically binds said OmpC autoantibody in (b), the presence of the formed complex having the OmpC autoantibody being indicative of Crohn's Disease.

2. The assay system of claim 1, wherein said plate further comprises a control.

3. The assay system of claim 1, wherein said indicator secondary antibody is an enzyme-labeled antibody.

4. The assay system of claim 3, wherein said system further comprises a substrate for said enzyme-labeled antibody.

5. The assay system of claim 3, wherein a product of said substrate is chromogenic.

6. The assay system of claim 1, wherein said assay is performed to facilitate earlier and appropriate treatment for Crohn's Disease patients.

7. An assay kit for improving the diagnosis of Crohn's disease comprising:
  (a) a plate well containing an OmpC antigen, or reactive fragment thereof;
  (b) an enzyme-labeled anti IgA antibody; and
  (c) instructions that specifically detect for Crohn's Disease by detecting for the presence of a complex of said OmpC antigen in (a), said OmpC autoantibody, and said indicator secondary antibody that specifically binds said OmpC autoantibody in (b), the presence of the formed complex having the OmpC autoantibody being indicative of Crohn's Disease.

8. The assay kit of claim 7, wherein said kit comprises a control.

9. The assay kit of claim 7, wherein said enzyme-labeled anti-IgA antibody is an indicator secondary antibody.

10. The assay kit of claim 9, wherein said kit further comprises a substrate for said enzyme-labeled antibody.

11. The assay kit of claim 9, wherein a product of said substrate is chromogenic.

* * * * *

SEQUENCE LISTING

<160> NUMBER OF SEQ ID NOS: 3

<210> SEQ ID NO 1
<211> LENGTH: 367

<212> TYPE: PRT
<213> ORGANISM: Escherichia coli
<220> FEATURE:
<223> OTHER INFORMATION: outer membrane protein C (OmpC)

<400> SEQUENCE: 1

Met Lys Ser Lys Val Leu Ala Leu Leu Ile Pro Ala Leu Leu Ala Ala
1               5                   10                  15

Gly Ala Ala His Ala Ala Glu Val Tyr Asn Lys Asp Gly Asn Lys Leu
            20                  25                  30

Asp Leu Tyr Gly Lys Val Asp Gly Leu His Tyr Phe Ser Asp Asn Lys
        35                  40                  45

Asp Val Asp Gly Asp Gln Thr Tyr Met Arg Leu Gly Phe Lys Gly Glu
    50                  55                  60

Thr Gln Val Thr Asp Gln Leu Thr Gly Tyr Gly Gln Trp Glu Tyr Gln
65                  70                  75                  80

Ile Gln Gly Asn Ser Ala Glu Asn Glu Asn Asn Ser Trp Thr Arg Val
                85                  90                  95

Ala Phe Ala Gly Leu Lys Phe Gln Asp Val Gly Ser Phe Asp Tyr Gly
            100                 105                 110

Arg Asn Tyr Gly Val Val Tyr Asp Val Thr Ser Trp Thr Asp Val Leu
        115                 120                 125

Pro Glu Phe Gly Gly Asp Thr Tyr Gly Ser Asp Asn Phe Met Gln Gln
    130                 135                 140

Arg Gly Asn Phe Gly Ala Thr Tyr Arg Asn Thr Asp Phe Phe Gly Leu
145                 150                 155                 160

Val Asp Gly Leu Asn Phe Ala Val Gln Tyr Gln Gly Lys Asn Gly Asn
                165                 170                 175

Pro Ser Gly Glu Gly Phe Thr Ser Gly Val Thr Asn Asn Gly Arg Asp
            180                 185                 190

Ala Leu Arg Gln Asn Gly Asp Gly Val Gly Gly Ser Ile Thr Tyr Asp
        195                 200                 205

Tyr Glu Gly Phe Gly Ile Gly Gly Ala Ile Ser Ser Lys Arg Thr
    210                 215                 220

Asp Ala Gln Asn Thr Ala Ala Tyr Ile Gly Asn Gly Asp Arg Ala Glu
225                 230                 235                 240

Thr Tyr Thr Gly Gly Leu Lys Tyr Asp Ala Asn Asn Ile Tyr Leu Ala
                245                 250                 255

Ala Gln Tyr Thr Gln Thr Tyr Asn Ala Thr Arg Val Gly Ser Leu Gly
            260                 265                 270

Trp Ala Asn Lys Ala Gln Asn Phe Glu Ala Val Ala Gln Tyr Gln Phe
        275                 280                 285

Asp Phe Gly Leu Arg Pro Ser Leu Ala Tyr Leu Gln Ser Lys Gly Lys
    290                 295                 300

Asn Leu Gly Arg Gly Tyr Asp Asp Glu Asp Ile Leu Lys Tyr Val Asp
305                 310                 315                 320

Val Gly Ala Thr Tyr Tyr Phe Asn Lys Asn Met Ser Thr Tyr Val Asp
                325                 330                 335

Tyr Lys Ile Asn Leu Leu Asp Asp Asn Gln Phe Thr Arg Asp Ala Gly
            340                 345                 350

Ile Asn Thr Asp Asn Ile Val Ala Leu Gly Leu Val Tyr Gln Phe
        355                 360                 365

<210> SEQ ID NO 2
<211> LENGTH: 302
<212> TYPE: DNA

```
<213> ORGANISM: Unknown
<220> FEATURE:
<223> OTHER INFORMATION: endogenous micro-organism from the human
      intestinal lumen
<220> FEATURE:
<221> NAME/KEY: CDS
<222> LOCATION: (2)...(301)
<223> OTHER INFORMATION: microbial I-2 polypeptide

<400> SEQUENCE: 2 a gat ctg gcc agc gcc gtg ggc atc cag tcc ggc agc atc ttt cat cac      49
  Asp Leu Ala Ser Ala Val Gly Ile Gln Ser Gly Ser Ile Phe His His
  1               5                  10                  15 ttc aag agc aag gat gag ata ttg cgt gcc gtg atg gag gaa acc atc       97
Phe Lys Ser Lys Asp Glu Ile Leu Arg Ala Val Met Glu Glu Thr Ile
                20                  25                  30 cat tac aac acc gcg atg atg cgc gct tca ctg gag gag gcg agc acg      145
His Tyr Asn Thr Ala Met Met Arg Ala Ser Leu Glu Glu Ala Ser Thr
        35                  40                  45 gtg cgc gaa cgc gtg ctg gcg ctg atc cgc tgc gag ttg cag tcg atc      193
Val Arg Glu Arg Val Leu Ala Leu Ile Arg Cys Glu Leu Gln Ser Ile
    50                  55                  60 atg ggc ggc agt ggc gag gcc atg gcg gtg ctg gtc tac gaa tgg cgc      241
Met Gly Gly Ser Gly Glu Ala Met Ala Val Leu Val Tyr Glu Trp Arg
65                  70                  75                  80 tcg ctg tcg gcc gaa ggc cag gcg cac gtg ctg gcc ctg cgt gac gtg      289
Ser Leu Ser Ala Glu Gly Gln Ala His Val Leu Ala Leu Arg Asp Val
                85                  90                  95 tat gag cag atc t                                                    302
Tyr Glu Gln Ile
            100

<210> SEQ ID NO 3
<211> LENGTH: 100
<212> TYPE: PRT
<213> ORGANISM: Unknown
<220> FEATURE:
<223> OTHER INFORMATION: microbial I-2 polypeptide

<400> SEQUENCE: 3

Asp Leu Ala Ser Ala Val Gly Ile Gln Ser Gly Ser Ile Phe His His
1               5                  10                  15

Phe Lys Ser Lys Asp Glu Ile Leu Arg Ala Val Met Glu Glu Thr Ile
                20                  25                  30

His Tyr Asn Thr Ala Met Met Arg Ala Ser Leu Glu Glu Ala Ser Thr
        35                  40                  45

Val Arg Glu Arg Val Leu Ala Leu Ile Arg Cys Glu Leu Gln Ser Ile
    50                  55                  60

Met Gly Gly Ser Gly Glu Ala Met Ala Val Leu Val Tyr Glu Trp Arg
65                  70                  75                  80

Ser Leu Ser Ala Glu Gly Gln Ala His Val Leu Ala Leu Arg Asp Val
                85                  90                  95

Tyr Glu Gln Ile
            100
```